US010028972B2

United States Patent
Roy et al.

(10) Patent No.: US 10,028,972 B2
(45) Date of Patent: *Jul. 24, 2018

(54) PHARMACEUTICAL COMPOSITIONS OF ANTI-ACNE AGENTS

(75) Inventors: Sunilendu Bhushan Roy, Gujarat (IN); Jay Shantilal Kothari, Gujarat (IN); Shafiq Sheikh, Gujarat (IN); Jinesh Suresh Pancholi, Gujarat (IN); Jitendra Dasharathlal Patel, Gujarat (IN); Ravindra Mittal, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 134 days.

This patent is subject to a terminal disclaimer.

(21) Appl. No.: 13/880,187

(22) PCT Filed: Oct. 19, 2011

(86) PCT No.: PCT/IN2011/000723
§ 371 (c)(1),
(2), (4) Date: Jul. 2, 2013

(87) PCT Pub. No.: WO2012/053013
PCT Pub. Date: Apr. 26, 2012

(65) Prior Publication Data
US 2013/0280308 A1    Oct. 24, 2013

(30) Foreign Application Priority Data

Oct. 21, 2010  (IN) .......................... 2935/MUM/2010
Jul. 28, 2011  (IN) .......................... 2153/MUM/2011

(51) Int. Cl.
| | | |
|---|---|---|
| A61K 9/107 | (2006.01) | |
| A61K 31/7056 | (2006.01) | |
| A61K 9/00 | (2006.01) | |
| A61K 9/06 | (2006.01) | |
| A61K 31/192 | (2006.01) | |
| A61K 45/06 | (2006.01) | |
| A61K 47/32 | (2006.01) | |
| A61K 47/44 | (2017.01) | |

(52) U.S. Cl.
CPC ........ *A61K 31/7056* (2013.01); *A61K 9/0014* (2013.01); *A61K 9/06* (2013.01); *A61K 9/1075* (2013.01); *A61K 31/192* (2013.01); *A61K 45/06* (2013.01); *A61K 47/32* (2013.01); *A61K 47/44* (2013.01); *Y10T 428/2982* (2015.01)

(58) Field of Classification Search
CPC ...... A61K 9/0014; A61K 9/06; A61K 9/1075; A61K 31/192; Y10T 428/2982
See application file for complete search history.

(56) References Cited

U.S. PATENT DOCUMENTS 6,113,921 A * 9/2000 Friedman et al. ............ 424/400

FOREIGN PATENT DOCUMENTS

WO    2010/096868 A1    9/2010

OTHER PUBLICATIONS

Cunliffe et al, Title: Title: A randomized, double-blind comparison of a clindamycin phosphate/benzoyl peroxide gel formulation and a matching clindamycin gel with respect to microbiologic activity and clinical efficacy in the topical treatment of acne vulgaris; Clinical Therapeutics, vol. 24, Issue 7, pp. 1117-1133, Published Jul. 2002.*
Synonyms.com; title: emulsifer; downloaded from www.synonym.com/synonyms/emulsifier on Aug. 26, 2016.*
Agrawal et al.; Title: development, evaluation and clinical stidies of Acitretin loaded nanostrutured lipid carriers for topical treatment of psoriasis; International Journal of Pharmaceutics; 401, pp. 93-102, published online Sep. 19, 2011).*
Author: FDA, title: CFR_Code of Federal Regulations Title 21, vol. 31, revised Apr. 1, 2017.*
Varaporn Buraphacheep Junyaprasert, et al: "Enhancement of the skin permeation of clindamycin phosphate by Aerosol OT/1-butanol microemulsions", Drug Development and Industrial Pharmacy, New York, NY, US, vol. 33, No. 8, Aug. 1, 2007 (Aug. 1, 2007), pp. 874-880, XP008152562, ISSN: 0363-9045, DOI: 10.1080/03639040600975097  DOI:  http://dx.doi.org/10.1080/03639040600975097.
Date A A et al: "Novel drug delivery systems: Potential in improving topical delivery of antiacne agents", Skin Pharmacology and Physiology: Journal of Pharmacological Andbiophysical Research, S. Karger AG, Basel, CH, vol. 19, No. 1, Dec. 1, 2005 (Dec. 1, 2005), pp. 2-16, XP008152560, ISSN: 1660-5527, DOI: 10.1159/000089138 DOI: http://dx.doi.org/10.1159/000089138.

* cited by examiner

Primary Examiner — Yanzhi Zhang
(74) Attorney, Agent, or Firm — Ladas & Parry LLP

(57) ABSTRACT

The present invention relates to pharmaceutical compositions for treatment of acne. In particular, the present invention relates to stable pharmaceutical compositions for treatment of acne along with other pharmaceutically acceptable excipients. These compositions exhibit excellent stability, greater permeability, and enhanced therapeutic efficacy. The invention also relates to processes for the preparation of such compositions.

7 Claims, 4 Drawing Sheets

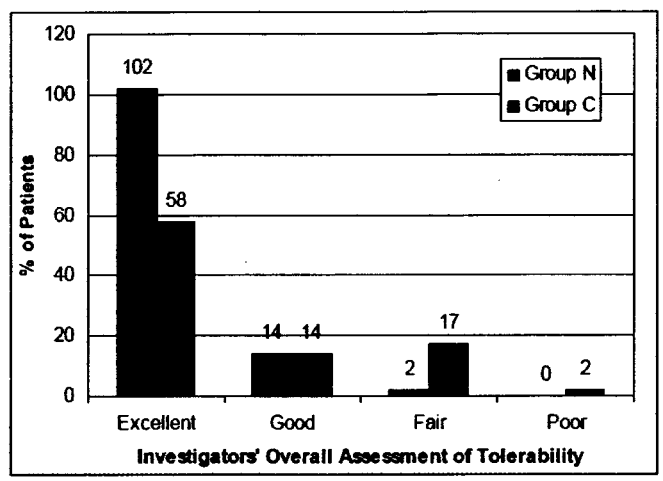
N = Nano-emulsion gel, C = Conventional gel, Group N: n = 118, Group C: n = 91
Figure 1: Overall assessment of tolerability at the end of the study.
Figure 2 (a): Electron micrograph of Sample 1

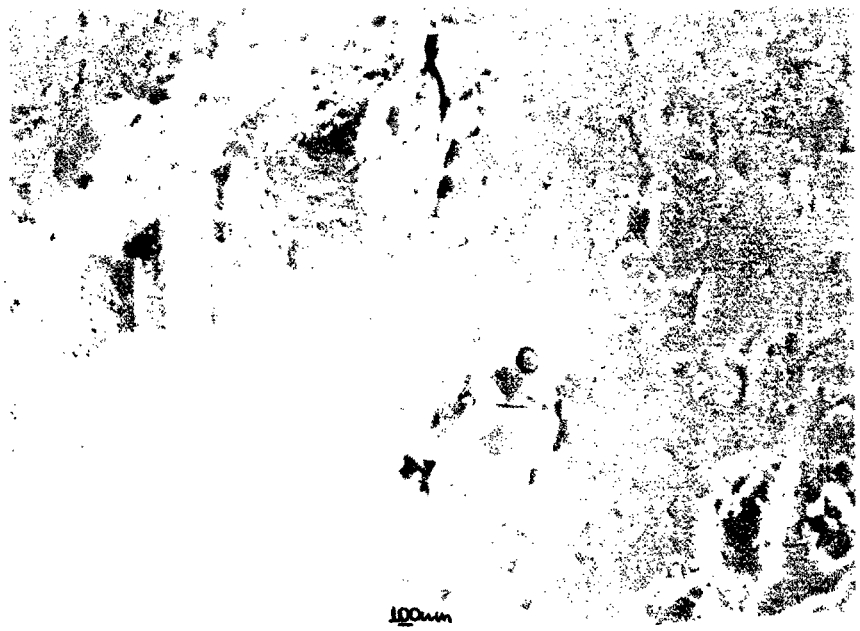
Figure 2 (b): Electron micrograph of Sample 2
Figure 2 (c): Electron micrograph of Sample 3

Figure 2 (d): Electron micrograph of Sample 4
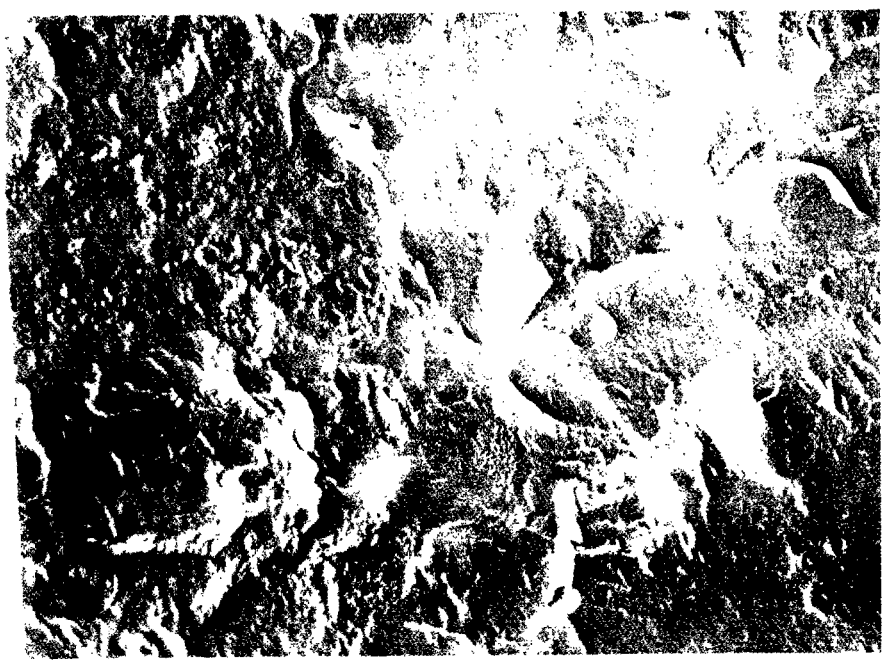
Figure 2 (e): Electron micrograph of Sample 5

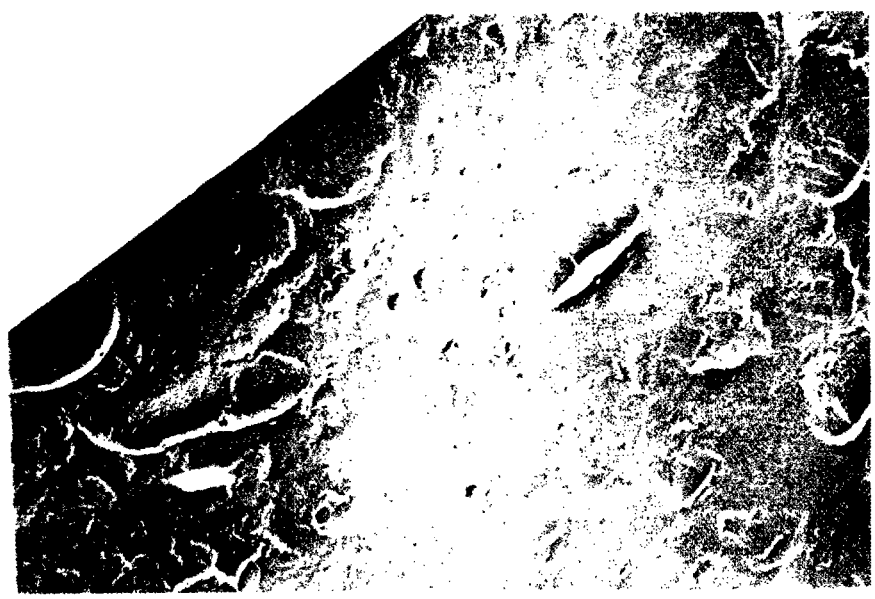
Figure 2 (f): Electron micrograph of Sample

PHARMACEUTICAL COMPOSITIONS OF ANTI-ACNE AGENTS

RELATED APPLICATION INFORMATION

This application is a 371 of International Application PCT/IN2011/000723 filed 19 Oct. 2011 entitled "Pharmaceutical Compositions Of Anti-Acne Agents", which was published in the English language on 26 Apr. 2012, with International Publication Number WO 2012/053013 A2 and which claims priority from Indian Patents Applications 2935/MUM/2010, filed 21 Oct. 2010 and 2153/MUM/2011 filed 28 Jul. 2011, the content of which are incorporated herein by reference.

FIELD OF THE INVENTION

The present invention relates to pharmaceutical compositions for treatment of acne. In particular, the present invention relates to stable pharmaceutical compositions for treatment of acne along with other pharmaceutically acceptable excipients. These compositions exhibit excellent stability, greater permeability, and enhanced therapeutic efficacy. The invention also relates to processes for the preparation of such compositions.

BACKGROUND OF THE INVENTION

Acne vulgaris is a skin condition that affects over 85% of all people. Acne is a term for a medical condition of plugged pores typically occurring on the face, neck, and upper torso. Following are four primary factors that lead to the formation of acne vulgaris; (1) increased sebum output resulting in oily, greasy skin; (2) increased bacterial activity normally due to an overabundance of *Propionibacterium acnes* bacteria; (3) plugging (hypercornification) of the follicle or pilosebaceous duct; and (4) production of inflammation by substances leaking into the dermis which cause inflammatory reactions. The plugged pores result in blackheads, whiteheads, pimples or deeper lumps such as cysts or nodules. Severe cases of acne can result in permanent scarring or disfiguring.

Acne occurs when the oil glands of the skin called sebaceous glands produce an increased amount of oil. The sebaceous glands are connected to canals in the skin called hair follicles that terminate in openings in the skin called pores. The increased amount of oil secreted by the sebaceous glands is caused by an increase in androgen hormones in both males and females during adolescence or puberty. Accompanying the increase in the amount of oil secreted by the sebaceous glands is an increase in the shedding of the skin lining the hair follicles. The increase in the amount of secreted oil in combination with the increase in the shedding of the skin lining the hair follicles increases the likelihood of the pores being clogged by the shedding skin. A pore clogged by the shedding skin is referred to as a comedo.

The *Propionibacterium acnes* (*P. acnes*) normally reside on the skin. The *propionibacterium acnes* invade the clogged follicles and grow in the mixture of oil and cells in the hair follicle. It produces chemicals that stimulate inflammation resulting in acne. Acne lesions range in severity from blackheads, whiteheads and pimples to more serious lesions such as deeper lumps, cysts and nodules.

In many instances, the inflammation within the acne lesion provides an opportunity for secondary infections to invade and grow in the inflamed hair follicle. Some of these secondary infections can be more serious and more resistant to treatment than the primary *Propionibacterium acnes* infection.

Various products and methods are currently available for treatment of acne. The only products that have anti-sebum activity are estrogens and 13 cis-retinoic acid (isotretinoin) and these must be used systemically to be effective. Isotretinoin is used to treat only severe cystic or conglobate acne (Anja Thielitz et al., *JDDG*, 6, 2008, Pp: 1023-1031). Because of its teratogenic properties, birth defects can occur. Isotretinoin is a powerful drug and can elevate triglycerides, total cholesterol and decrease high-density lipoproteins (HDL). Other side effects include dry skin, dry eyes, itching, headaches, nosebleed, and photosensitivity. It is generally taken for 4-5 months to see improvement. However, all topical retinoic acid preparations may be irritating, and this may contribute to underutilization in clinical practices (Cynthia E Irby et al., *J. of Adolescent Health*, 43, 2008, Pp-421-424). Recently, one brand of oral contraceptive has been approved for the treatment of acne for patients who request birth control.

A number of topical and systemic agents are used to lower the number of bacteria that colonize the follicular duct. These include benzoyl peroxide (BP), and BP (5%), erythromycin (3%) combination (Benzamycin®). BP has antibacterial activity and drying effects and is available over the counter or by prescription. BP is applied once or twice daily for 1-2 months. BP can produce erythema and peeling of skin. BP is often tried first for both non-inflammatory and mild inflammatory acne. Other topical antibiotics include clindamycin and erythromycin. It is known that the combination of topical antibiotic such as clindamycin with other topical agents is more therapeutically effective than either drug used alone (James Q. Del Rosso et al., *Drug therapy Topics*, Volume 85; January 2010, Pp: 15-24). These topical antibiotics are used as solutions, lotions or gels by prescription only. Usually they are applied once or twice daily and results are seen in 1-2 months. Another topical agent, azelaic acid 20% (Azelex®) also has mild antibacterial effects.

Systemic antibiotics include tetracycline and its analogs, which are used in low doses for years or until the end of the acne prone years. Most patients with mild inflammatory acne receive a combination of topical antibiotics and tretinoin or other retinoid. Application of topical antibiotic such as clindamycin gel after the pretreatment of skin with topical retinoid such as adapalene gel may contribute significantly to the increased efficacy of therapy (Gaurav K. Jain et al., *Indian J Dermatol Venereol Leprol*, September-October 2007, Vol-73(5), Pp: 326-329). Several clinical studies have also been performed earlier which demonstrates improved efficacy and tolerability of topical antibiotics and topical retinoids (John E. Wolf E. et al., *J Am Acad Dermatol*, 2009, Vol-49(3), Pp-S211-S217, and J. Z. Jhang et al., *J of Derm Treat*, 2004, Vol-15, Pp-372-378). Bacterial resistance does occur so antibiotics may be changed or BP is substituted since resistance does not occur with BP. More severe acne requires systemic antibiotics and topical retinoid. The most severe must receive oral isotretinoin for 4-5 months.

Various topical products containing combination of clindamycin phosphate and adapalene are available in market. For example, Deriva-CMS® Gel [marketed by Glenmark Pharmaceuticals Ltd.], Achilles®-C Gel [marketed by Sandoz Ltd.], Adaple®-C Gel [marketed by Wallace Pharmaceuticals Ltd.], Zudenina®-Plus Gel [marketed by Roemmers SAICF], Medapine®-AC Gel [marketed by Daiichi-Sankyo Co. Ltd.], and Faceclin®-A Gel [marketed by Piramal].

There are no drugs that directly affect the inflammatory acne. The retinoids do have some anti-inflammatory properties, but these are poorly described. Topical steroid and even systemic steroids have been used to abort a severe flare of fulminant acne, but these are limited uses because of the side effects. Benzoyl peroxide gels are sometimes used as first aid on acne lesions. These function as a "drawing poultice", but data supporting this use is not available.

The treatment for acne centers around opening the pore, killing *P. acnes*, reducing sebum production and regulating inflammatory responses. Retinoids are the agents to reduce sebum production and open the pore. As a topical agent, adapalene (Differin®) or tretinoin (Retin-A®) is used for mild and moderate acne.

It is often advantageous to be able to deliver the drug over a period of time, such that a desired level of the drug in the target tissue is achieved for a period of time sufficient to achieve the desired result, e.g., killing most of a population of infectious bacterial. Dermatological conditions, such as acne, require multiple delivery strategies because they have multiple delivery requirements, such as killing skin surface bacteria while also penetrating deep into inflamed sebaceous glands to kill bacteria in that locus.

U.S. Patent Publication No. 2010/0015216 discloses composition for the treatment of acne comprising: a first therapeutic agent selected from the group consisting of salicylic acid, azelaic acid, adapalene, benzoyl peroxide, antibiotics and combinations thereof; and a second therapeutic agent which comprises a taurine species.

U.S. Pat. No. 5,962,571 discloses a pharmaceutical composition for the treatment of acne having an acne reduction component in an amount sufficient to reduce the redness and blemishes associated with acne.

U.S. Patent Publication No. 2010/0029781 discloses a method of preparing a solvent-microparticle (SMP) topical gel formulation comprising a bioactive drug wherein the formulation comprises the drug dissolved in a liquid and the drug in a microparticulate solid form dispersed in the liquid.

U.S. Patent Publication No. 2010/0068284 discloses a stable fixed dose topical formulation comprising therapeutically effective amounts of adapalene-containing microparticles and clindamycin. However, such formulation may not significantly reduce the incident and severity of acne lesions.

U.S. Pat. No. 5,629,021 discloses micellar nanoparticles and methods of their production.

U.S. Pat. No. 5,894,019 discloses topical compositions comprising lipid and essentially free of emulsifiers and surfactants.

European Patent No. EP 0671903 B discloses topical compositions in the form of submicron oil spheres.

Most of the topical preparations contain vehicles comprising permeation enhancers, solvents, and high amount of surfactants to achieve topical compositions for acne treatment. But use of these agents is harmful, especially in chronic application, as many of them cause undesirable effects such as irritation and dryness and resulting in poor patient tolerability.

In general, current products are effective in reducing the clinical observation of acne but it does not completely eliminate the condition, hence the consumer is not completely satisfied with results of these products.

Although various over-the-counter products are commercially available to counteract acne condition, such as anti-acne agents for topical use, including salicylic acid, sulfur, lactic acid, glycolic acid, pyruvic acid, urea, resorcinol, N-acetylcysteine, retinoic acid, isotretinoin, tretinoin, adapalene, tazoretene, antibacterials such as clindamycin and erythromycin, vitamins such as zinc, folic acid and nicotinamide, benzoyl peroxide, octopirox, triclosan, azelaic acid, phenoxyethanol, phenoxypropanol, and flavinoids, however, these agents tend to lack in potential to mitigate the acne condition and may have negative side effects when devised in conventional topical formulations.

Therefore, despite of the wide availability of products for acne, there exists a need to develop suitable topical preparations which facilitate drug permeation through the skin, exhibiting enhanced therapeutic activity and mitigating instance and severity of adverse events resulting from topical use of anti-acne agents. The topical preparation also ought to render improved tolerability to ensure successful acne therapy.

SUMMARY OF THE INVENTION

In one general aspect there is provided a stable topical pharmaceutical composition comprising nano size droplets of one or more anti-acne agent/s or salts thereof.

In one general aspect there is provided a stable topical pharmaceutical composition comprising nano size droplets of clindamycin or salts thereof.

In one general aspect there is provided a stable topical pharmaceutical composition comprising nano size droplets of clindamycin and one or more anti-acne agent/s or salts thereof.

In another general aspect there is provided a stable topical pharmaceutical composition comprising nano size droplets of clindamycin and adapalene or salts thereof.

In another general aspect there is provided a stable topical pharmaceutical composition comprising nano size droplets of clindamycin and adapalene or salts thereof, wherein the amount of adapalene or salt thereof in the composition ranges from about 0.01% to about 0.3% w/w of and the amount of clindamycin or salt thereof in the composition ranges from about 0.5% to about 5.0% w/w of the composition.

In another general aspect there is provided a stable topical pharmaceutical composition comprising nano size droplets of one or more anti-acne agent/s or salts thereof, wherein said composition comprises oil in amount ranging from about 5 to about 25% w/w of the composition.

In another general aspect there is provided a stable topical pharmaceutical composition comprising nano size droplets of one or more anti-acne agent/s or salts thereof, wherein said composition comprises one or more emulsifier/s in amount ranging from about 0.1 to about 10% w/w of the composition.

In another general aspect there is provided a stable topical pharmaceutical composition comprising nano size droplets of one or more anti-acne agents or salts thereof, wherein said composition comprises one or more emulsifier/s and oil in the weight ratio ranging from about 0.1:20 to about 0.1:1.

Embodiments of the pharmaceutical composition may include one or more of the following features. The pharmaceutical composition further may include one or more pharmaceutically acceptable excipients. For example, the pharmaceutically acceptable excipients may include one or more of lipids, oils, emulsifiers or surfactants, pH adjusting agents, emollients, humectants, preservatives, chelating agents, thickening agent, and the like.

In another general aspect there is provided a stable topical pharmaceutical composition comprising nano size droplets of one or more anti-acne agents or salts thereof, wherein the composition retains at least 80% potency of said anti-acne agent or salt thereof after storage for 3 months at 40° C. and 75% relative humidity.

$D_{90}$ particle size of droplets of anti-acne agent or salts thereof in the composition of the invention is less than about 500 nm, preferably about 250 nm, and more preferably about 100 nm.

Embodiments of the pharmaceutical composition may include one or more of the following features. The pharmaceutical composition further may include one or more pharmaceutically acceptable excipients. For example, the pharmaceutically acceptable excipients may include one or more of lipids, oils, emulsifiers or surfactants, pH adjusting agents, emollients, humectants, preservatives, chelating agents, thickening agent, and the like.

In another general aspect there is provided a stable topical pharmaceutical composition prepared by the process comprising:
a) combining an oily phase comprising one or more anti-acne agents or salts thereof along with other pharmaceutically acceptable excipients with an aqueous phase to form an emulsion;
b) reducing the particle size of emulsion of step a) to a droplet size having $D_{90}$ particle size of less than about 500 nm; and
c) mixing other pharmaceutically acceptable excipients to emulsion obtained in step b) and converting it into a suitable finished dosage form.

Embodiments of the pharmaceutical composition may include one or more of the following features. The pharmaceutical composition further may include one or more pharmaceutically acceptable excipients. For example, the pharmaceutically acceptable excipients may include one or more of lipids, oils, emulsifiers or surfactants, pH adjusting agents, emollients, humectants, preservatives, chelating agents, thickening agent, and the like.

In another general aspect there is provided a method for improving the local and systemic tolerability of anti-acne agents comprising administering a stable topical pharmaceutical composition comprising nano size droplets of one or more anti-acne agents or salts thereof.

The details of one or more embodiments of the invention are set forth in the description below. Other features, objects and advantages of the invention will be apparent from the description and claims.

BRIEF DESCRIPTION OF DRAWINGS

FIG. 1: Overall assessment of tolerability at the end of the study.
FIG. 2(a): Electron micrograph of Sample 1
FIG. 2(b): Electron micrograph of Sample 2
FIG. 2(c): Electron micrograph of Sample 3
FIG. 2(d): Electron micrograph of Sample 4
FIG. 2(e): Electron micrograph of Sample 5
FIG. 2(f): Electron micrograph of Sample 6

DETAILED DESCRIPTION OF THE INVENTION

The inventors of the invention have surprisingly found that when anti-acne agents or salts thereof are formulated into nano size droplets in pharmaceutically acceptable emulgel (emulsion gel) system which includes optimized ratios of oils and/or emulsifiers, the composition exhibits enhanced therapeutic efficacy and also the composition is well tolerated (both locally and systemically) for the treatment of acne vulgaris.

Further, the inventors have found that advantageously the composition possess stable thermodynamic properties and do not have the problems of creaming, flocculation, coalescence or sedimentation, which are commonly associated with macro-emulsion, thus ensuring better stability and longer shelf-life of the resulting product.

Moreover, the composition of the invention results in immediate and sustained action, covering large surface area with less quantity and posses good spreadability. The composition is also non-irritant to skin and mucous membranes, requires reduced frequency of application, thus leading to improved patient compliance and offers cosmetic benefits like non-stickiness, and non-greasy feel.

The term "acne" includes inflammatory diseases of the pilosebaceous follicles and/or skin glands, and commonly is characterized by papules, pustules, cysts, nodules, comedones, other blemishes or skin lesions. The term "acne" as used herein includes all known types of acne. Some types of acne which can be treated with the composition of the present invention are, for example, acne vulgaris, acne comedo, papular acne, premenstrual acne, preadolescent acne, acne venenata, acne cosmetica, pomade acne, acne detergicans, acne excoriee, gram negative acne, pseudofolliculitis barbae, folliculitis, perioral dermatitis, hiddradenitis suppurativa, cystic acne, acne atrophica, bromide acne, chlorine acne, acne conglobata, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, nodulocystic acne and acne rosacea.

The embodiments of the present invention relate to a topical pharmaceutical composition which comprises one or more anti-acne agents or salts thereof in the form of nano size droplets, such as a non-gel emulsion.

In a preferred embodiment, the nano size droplets of anti-acne agents or salts thereof posses a $D_{90}$ particle size of less than about 500 nm.

In a further embodiment, the nano size droplets of anti-acne agents or salts thereof posses a $D_{90}$ particle size of less than or equal to about 250 nm, and more preferably less than or equal to about 100 nm.

In a further embodiment, the composition of the present invention is stable and retains at least 80% potency of anti-acne agent when stored for at least three months at 40° C. and 75% relative humidity.

In a yet another embodiment, the topical pharmaceutical composition exhibits excellent local and systemic tolerability to anti-acne agents when administered in the form of nano sized droplets.

Anti-acne agent for the purpose of the present invention may be selected from, but not limited to one or more of adapalene, azelaic acid, benzoyl peroxide, salicylic acid, sulfur, lactic acid, glycolic acid, pyruvic acid, urea, resorcinol, N-acetylcystein, retinoic acid, octopirox, triclosan, phenoxyethanol, phenoxypropanol, clindamycin, erythromycin, tretinoin, isotretinoin, sodium sulfacetamide, tazarotene, spirinolacton, or salts thereof.

In a preferred embodiment, the composition comprises nano size droplets of clindamycin or salts thereof.

In a further preferred embodiment, the composition comprises a combination of at least two anti-acne agents or salts thereof.

In an embodiment the composition comprises a combination of clindamycin and adapalene or salts thereof.

In another embodiment, the weight ratio of adapalene to clindamycin in the composition ranges from about 1:5 to about 1:15.

In a further embodiment, the composition comprises about 0.5% to about 5.0% w/w, and preferably about 1.0% w/w of clindamycin or salt thereof (based on 100% total weight of the composition).

In a further embodiment, the composition comprises about 0.01% to about 0.3% w/w, and preferably about 0.1% w/w of adapalene or salt thereof (based on 100% total weight of the composition).

The composition of the present invention further comprises one or more pharmaceutically acceptable excipients selected from, but not limited to lipids, oils, emulsifiers/surfactants, initiators, pH adjusting agents, emollients, humectants, preservatives, and chelating agents.

The pH of the composition of the invention ranges from about 4.5 to about 7.0, and preferably from 5.0 to about 6.5.

Suitable lipids which can be used include one or more of hydrocarbons, fatty alcohols, fatty acids, glycerides or esters of fatty acids with $C_1$-$C_{36}$ alkanols. Hydrocarbons may include paraffin or petroleum jelly. Fatty alcohols may include decanol, dodecanol, tetradecanol, hexadecanol or octadecanol. Fatty acids may include $C_6$-$C_{24}$ alkanoic acids such as hexanoic acid, octanoic acid, decanoic acid, dodecanoic acid, tetradecanoic acid, hexadecanoic acid, octadecanoic acid, unsaturated fatty acids such as oleic acid and linoleic acid. Glycerides may include olive oil, castor oil, sesame oil, caprylic/capric acid triglyceride or glycerol mono-, di- and tri-esters with palmitic and/or stearic acid. Esters of fatty acids may include $C_1$-$C_{36}$ alkanols such as beeswax, carnauba wax, cetyl palmitate, lanolin, isopropyl myristate, isopropyl stearate, oleic acid decyl ester, ethyl oleate and $C_6$-$C_{12}$ alkanoic acid esters and the like.

Suitable oils may include one or more of almond oil, apricot seed oil, borage oil, canola oil, coconut oil, corn oil, cotton seed oil, fish oil, jojoba bean oil, lard oil, linseed oil, boiled macadamia nut oil, mineral oil, olive oil, peanut oil, safflower oil, sesame oil, soybean oil, squalane, sunflower seed oil, tricaprylin (1,2,3 trioctanoyl glycerol), wheat germ oil and the like. The preferred quantity of oil used is in the range of about 5 to about 25% w/w, and more preferably in the range of about 5% to about 20% w/w of the composition.

Suitable emulsifiers/surfactant may include one or more of ionic polysorbate surfactant, Tween® 20, Tween® 40, Tween® 60, Tween® 80, Nonylphenol Polyethylene Glycol Ethers, (alkylphenol-hydroxypolyoxyethylene), Poly(oxy-1, 2-ethanediyl), alpha-(4-nonylphenol)-omega-hydroxy-, branched (i.e. Tergitol® NP-40 Surfactant), Nonylphenol Polyethylene Glycol Ether mixtures (i.e. Tergitol® NP-70 (70% AQ) Surfactant), phenoxypolyethoxyethanols and polymers thereof such as Triton®, Poloxamer®, Spans®, Tyloxapol®, different grades of Brij, sodium dodecyl sulfate and the like. The preferred quantity of the emulsifiers/surfactant used is in the range of about 0.1% to about 10% w/w of the composition.

In a preferred embodiment, the ratio of emulsifier or surfactant to oil in the pharmaceutical composition of the present invention ranges from about 0.1:20 to about 0.1:1, preferably about 0.1:10 to about 0.1:1.

Suitable pH adjusting agents which can be used include one or more of organic or inorganic acids and bases including sodium hydroxide, potassium hydroxide, ammonium hydroxide, phosphate buffers, citric acid, acetic acid, fumaric acid, hydrochloric acid, malic acid, nitric acid, phosphoric acid, propionic acid, sulfuric acid, tartaric acid and the like.

Suitable emollients which can be used include one or more of caprylic/capric triglycerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, glyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, steareth-2 or -100, stearic acid, stearyl alcohol, urea and the like.

Suitable preservatives which can be used include one or more of phenoxyethanol, parabens (such as methylparaben and propylparaben), propylene glycols, sorbates, urea derivatives (such as diazolindinyl urea), and the like.

Suitable humectants which can be used include one or more of propylene glycol, glycerin, butylene glycol, sorbitol, triacetin and the like.

Suitable chelating agents which can be used include one or more of disodium EDTA, edetate trisodium, edetate tetrasodium, diethyleneamine pentaacetate and the like.

Suitable initiators which can be used include one or more of alcohols like $C_1$-$C_{12}$ alcohols, diols and triols, glycerol, methanol, ethanol, propanol, octanol and the like.

In one embodiment, composition of the invention may be prepared by a) combining an oily phase comprising one or more anti-acne agents or salts thereof along with other pharmaceutically acceptable excipients with an aqueous phase to form an emulsion; b) reducing the particle size of emulsion of step a) to a droplet size having $D_{90}$ particle size of less than about 500 nm; and c) mixing other pharmaceutically acceptable excipients to emulsion obtained in step b) and converting it into a suitable finished dosage form.

The nano size droplets may be produced with reciprocating syringe instrumentation, continuous flow instrumentation, high speed mixing or high pressure homogenization. However, it will be appreciated to the person skilled in the art any known method of reducing the size of droplet may be adopted to serve the purpose of the present invention.

Small droplets of the nano emulsion may be formed by passing the emulsion through a homogeniser under different pressures ranging from 3,500-21,500 psi. The emulsion may be passed between 4-5 times under the same conditions to get a final $D_{90}$ droplet size of less than about 500 nm. The nano droplets formed may be filtered through 0.2 to 0.4 micron filter.

The gel base may be used in the present invention to form a gel matrix for the preparation of nanogel from nanoemulsion. The gel base comprises of one or more of thickening agents.

Suitable thickening agents which can be used include one or more of cellulose polymer, a carbomer polymer, a carbomer derivative, a cellulose derivative, polyvinyl alcohol, poloxamers, polysaccharides and the like.

Suitable dosage form of the invention may include cream, gel, ointment, lotion, liniment, paste, and emulsion.

In a preferred embodiment, the composition of the invention is in the form of gel.

The present invention further provides use of a pharmaceutical composition comprising one or more anti-acne agents or salts thereof in the form of nano size droplets for improving the tolerability to anti-acne agents for the treatment of acne vulgaris.

The efficacy and safety of the composition of the present invention was evaluated vis-à-vis other conventional gel formulation.

In one study, efficacy and safety of the composition of the present invention (containing 0.1% adapalene and 1% clindamycin) was evaluated vis-à-vis other marketed gel formulation (Deriva-CMS® Gel [marketed by Glenmark Pharmaceuticals Ltd.] containing 0.1% adapalene micro-spheres and 1% clindamycin). Significantly better reductions in total (79.7 vs. 62.7%), inflammatory (88.7 vs. 71.4%) and non-inflammatory (74.9 vs. 58.4%) lesions were reported with the composition of the present invention as compared to the marketed formulation (P<0.001 for all). Mean acne severity score also reduced significantly more with the nano-emulsion formulation (1.9±0.9 vs. 1.4±1.0; P<0.001) than the comparator. Significantly lower incidence and lesser intensity of adverse events like local irriation (4.2% vs. 19.8%; P<0.05) & erythema (0.8% vs. 9.9%; P<0.05) were recorded with the composition of the present invention. FIG. 1 shows the overall assessment of the tolerability.

In another study, efficacy and safety of the composition of the present invention (containing 1% clindamycin phosphate) was evaluated vis-à-vis other marketed gel formulation (Clindac-A® Gel [marketed by Galderma International] containing 1% clindamycin phosphate). Reductions in inflammatory (73.4 vs. 60.6%; P<0.005) and total (69.3 vs. 51.9%; P<0.001) acne lesions were reported to be significantly greater with the composition of the present invention as compared to the marketed formulation. Significantly more reduction in the mean acne severity score was noticeable with the composition of the present invention (1.6±0.9 vs. 1.0±0.8; P<0.001) than the comparator. A comparable or slightly better safety profile of the composition of the present invention was reported.

Thus, it is concluded that the composition of the present invention is more effective in reducing total number and severity of lesions including inflammatory and non-inflammatory lesions and is better tolerated (both locally and systemically) than the marketed formulation. The composition of the present invention was also found to reduce the incidence and severity of adverse events resulting from its application when compared with the adverse events resulting from application of the marketed formulation.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

Example 1: Clindamycin Phosphate Nano Emulsion

TABLE 1

| Sr. No. | Ingredients | % w/w |
| --- | --- | --- |
| 1 | Clindamycin Phosphate | 1.00-4.00 |
| 2 | Polysorbate 80 | 4.00-8.00 |
| 3 | Glycerol | 7.00-13.00 |
| 4 | Soyabean oil | 14.00-20.00 |

TABLE 1-continued

| Sr. No. | Ingredients | % w/w |
| --- | --- | --- |
| 5 | Disodium EDTA | 0.05-1.50 |
| 6 | Vitamin E Acetate | 0.05-0.50 |
| 7 | Water | Q.S. |

Procedure:

Clindamycin phosphate was dissolved in water, polysorbate 80, glycerol, vitamin E acetate and soybean oil. The resulting blend was homogenized to reduce the droplet size to $D_{90}$ particle size of about 250 nm with the help of high pressure homogenization to get the nano emulsion.

Example 2: Clindamycin Phosphate Nanogel

TABLE 2

| Sr. No. | Ingredients | % w/w |
| --- | --- | --- |
| 1 | Clindamycin Phosphate | 1.2 |
| 2 | Adapalene | 0.1 |
| 3 | Polysorbate 80 | 3.0 |
| 4 | Glycerol | 5.0 |
| 5 | Soyabean oil | 9.0 |
| 6 | Carbopol 974P | 1.0 |
| 7 | Sodium Hydroxide | Q.S. |
| 8 | Water | Q.S. |

Procedure:

Clindamycin phosphate was dissolved in water, alcohol, polysorbate 80, glycerol and soybean oil. The resulting blend was homogenized to reduce the droplet size to $D_{90}$ particle size of about 250 nm by high pressure homogenization to get the nano emulsion. Adapalene was dispersed in alcohol and aqueous dispersion of carbopol 974P followed by suitable pH adjustment using Sodium hydroxide solution. The aqueous dispersion of carbopol 974P was mixed with nano emulsion to get nanogel.

Example 3: Clindamycin Phosphate Nanogel

TABLE 3

| Sr. No. | Ingredients | % w/w |
| --- | --- | --- |
| 1 | Clindamycin Phosphate | 0.50-3.00 |
| 2 | Alcohol | 3.00-7.00 |
| 3 | Polysorbate 80 | 1.00-5.00 |
| 4 | Glycerol | 3.00-7.00 |
| 5 | Soyabean oil | 7.00-11.00 |
| 6 | Disodium EDTA | 0.05-0.50 |
| 7 | Vitamin E Acetate | 0.05-0.50 |
| 8 | Carbopol 974P | 0.50-3.00 |
| 9 | Water | Q.S. |

Procedure:

Clindamycin phosphate was dissolved in water, alcohol, polysorbate 80, glycerol, soybean oil, vitamin E acetate and disodium EDTA. The resulting blend was homogenized to reduce the droplet size to $D_{90}$ particle size of about 250 nm with the help of high pressure homogenization to get the nano emulsion. Sodium hydroxide solution was added to aqueous dispersion of Carbopol 974P to adjust the pH and finally it was mixed with nano emulsion to get nanogel.

Example 4: Clindamycin Phosphate Nano Emulsion

TABLE 4

| Sr. No. | Ingredients | Quantity % w/w |
|---|---|---|
| 1 | Clindamycin Phosphate | 1.200 |
| 2 | Polysorbate 80 | 3.000 |
| 3 | Glycerol | 5.000 |
| 4 | Soybean oil | 9.000 |
| 5 | Disodium EDTA | 0.250 |
| 6 | Vitamin E Acetate | 0.100 |
| 7 | Carbopol 974P | 1.500 |
| 8 | Sodium Hydroxide | 0.332 |
| 7 | Water | Q.S. |

Procedure:

Clindamycin phosphate was dissolved in water, polysorbate 80, glycerol, soybean oil, vitamin E acetate and disodium EDTA. The resulting blend was homogenized to reduce the droplet size to $D_{90}$ particle size of about 250 nm with the help of high pressure homogenization to get the nano emulsion. Sodium hydroxide solution was added to aqueous dispersion of Carbopol 974P to adjust the pH and finally it was mixed with nano emulsion to get nanogel.

Example 5: Freeze-Fracture Electron Microscopy of the Nanogel Composition

Preparation Procedure—

For freeze-fracture electron microscopy, the samples (total 6) of nanogel composition were quenched using sandwich technique and liquid nitrogen-cooled propane. Using this technique a cooling rate of 10,000 Kelvin per second is reached avoiding ice crystal formation and artifacts possibly caused by the cryofixation process. The cryo-fixed sample was stored in liquid nitrogen for less than 2 hours before processing. The fracturing process was carried out in JEOL JED-9000 freeze-etching equipment and the exposed fracture planes were shadowed with Pt for 30 sec in an angle of 25-35 degree and with carbon for 35 sec (2 kV/60-70 mA, $1 \times 10^{-5}$ Torr). The replicas produced this way were cleaned with concentrated, fuming $HNO_3$ for 24 hours followed by repeating agitation with fresh chloroform/methanol (1:1 by vol.) at least 5 times. The replicas cleaned this way were examined at a JEOL 1200 EX transmission electron microscope.

Size distribution of nanogel droplets is summarized in Table 5.

TABLE 5

| Sr. No. | NEGATIVE # | ORIGINAL MAG. [K] | FINAL MAG. | 100 nm = X [mm] |
|---|---|---|---|---|
| 1 | Sample 1 | 13.1 | 39.150 | 3.9 |
| 2 | Sample 2 | 13.1 | 37.845 | 3.8 |
| 3 | Sample 3 | 13.1 | 44.370 | 4.4 |
| 4 | Sample 4 | 19.3 | 69.480 | 6.9 |
| 5 | Sample 5 | 19.3 | 57.900 | 5.8 |
| 6 | Sample 6 | 19.3 | 54.040 | 5.4 |

As visible from the electron micrographs of Sample 1 to 6 [FIG. 2(a) to 2(f) respectively] taken from several freeze-fracture preparations, the sample contains high concentration of fine substructures (below 20 nm in diameter). They appear frequently singular but also form larger superstructures (between 20 and 150 nm in diameter).

Example 6: Stability Study on Clindamycin Phosphate Nanogel Composition

TABLE 6

| | % Drug in the formulation | | | |
|---|---|---|---|---|
| Sr. No. | Initial | 1 Month | 2 Month | 3 Month |
| 1 | 100.6% | 101.80% | 100.60% | 93.1% |
| 2 | 102.7% | 101.6% | 96.8% | 98.5% |
| 3 | 108.2% | 105.5% | 100.7% | 99.2% |

Table 6 provides stability data of Clindamycin phosphate nanogel composition when stored at 40° C. and 75% relative humidity for three months and indicates that the composition remains stable and retains at least 80% potency of clindamycin phosphate over the storage period.

Example 7: Stability Study on Clindamycin Phosphate and Adapalene Nanogel Composition

TABLE 7

| | | % drug in the formulation | | | | | |
|---|---|---|---|---|---|---|---|
| Sr. No. | | Initial | 1 Month | 2 Month | 3 Month | 6 Month CRT | 9 Month CRT |
| 1 | Clindamycin | 100.5% | 96.70% | 98.6% | 96.0% | ND | ND |
| | Adapalene | 102.7% | 97.50% | 93.9% | 95.6% | ND | ND |
| 2 | Clindamycin | 101.8% | 100.40% | 96.4% | 95% | 98.90% | 95.35 |
| | Adapalene | 95.8% | 97.70% | 93.2% | 93.60% | 95.30% | 95.05 |
| 3 | Clindamycin | 100.2% | 97.70% | 98.5% | 95.8 | 97.60% | 96.85 |
| | Adapalene | 101.3% | 98.50% | 98.9% | 98.30% | 100.80% | 99.5 |

Table 7 provides stability data of Clindamycin phosphate and Adapalene nanogel composition when stored at 40° C. and 75% relative humidity for three months and at 20° C. and 60% relative humidity from sixth to nine months. The data indicates that the composition remains stable and retains at least 80% potency of clindamycin phosphate and adapalene over the storage period.

While the invention has been described in terms of its specific embodiments, certain modifications and equivalents will be apparent to those skilled in the art and are intended to be included within the scope of the invention.

We claim:

1. A stable topical pharmaceutical nanogel composition of clindamycin or a salt thereof, the nanogel composition consisting of a nanoemulsion and a gel base, the nanoemulsion consisting of nano size droplets of clindamycin or a salt thereof, 5% to 25% of oils, 0.1% to 10% of an emulsifier selected from a group consisting of ionic polysorbate surfactant, nonylphenol polyethylene glycol ethers, alkylphenol-hydroxypolyoxyethylene, poly(oxy-1,2-ethanediyl), alpha-(4-nonylphenol)-omega-hydroxy-, branched, nonylphenol polyethylene glycol ether mixtures, phenoxypolyethoxyethanols, and sodium dodecyl sulfate; and one or more pharmaceutically acceptable excipients consisting of initiators, pH adjusting agents, thickening agents, emollients, humectants, preservatives, and chelating agents.

2. The stable topical pharmaceutical composition of claim 1, wherein the nano size droplets of clindamycin or a salt thereof have a D90 particle size of 500 nm or less.

3. The stable topical pharmaceutical composition of claim 1, wherein the nano size droplets of clindamycin or a salt thereof have a D90 particle size of 250 nm or less.

4. The stable topical pharmaceutical composition of claim 1, wherein the nano size droplets of clindamycin or a salt thereof have a D90 particle size of 100 nm or less.

5. The stable topical pharmaceutical composition of claim 1, wherein the emulsifier and oil are present in the composition in a weight ratio of from 0.1:20 to 0.1:1.

6. The stable topical pharmaceutical composition of claim 1, wherein the composition retains at least 80% potency of the clindamycin or salt thereof after storage for 3 months at 40° C. and 75% relative humidity.

7. The stable topical pharmaceutical composition of claim 1, is prepared by a process comprising:
    a) combining an oily phase consisting of clindamycin or a salt thereof along with oils and the emulsifier with an aqueous phase to form an emulsion;
    b) reducing the particle size of the emulsion of step a) to a droplet size having a D90 particle size of 500 nm or less; and
    c) mixing the nanoemulsion obtained in step (b) with a